US005697381A

United States Patent [19]
Rantala et al.

[11] Patent Number: 5,697,381
[45] Date of Patent: Dec. 16, 1997

[54] MEASURING INSTRUMENT FOR DETECTING DEGREES OF RELAXATION

[75] Inventors: Börje Rantala, Helsinki; Kari Mäkiniemi, Espoo, both of Finland

[73] Assignee: Instrumentarium Oy, Finland

[21] Appl. No.: 499,118

[22] Filed: Jul. 6, 1995

[30] Foreign Application Priority Data

Jul. 7, 1994 [FI] Finland .................................. 943252

[51] Int. Cl.⁶ ...................................................... A61B 5/05
[52] U.S. Cl. ........................................ 128/774; 128/782
[58] Field of Search .............................. 128/734, 741, 128/782, 774

[56] References Cited

U.S. PATENT DOCUMENTS

| 4,236,528 | 12/1980 | Stanec et al. ............... 128/782 |
| 4,387,723 | 6/1983 | Atlee et al. . |
| 5,263,490 | 11/1993 | Hayes et al. . |
| 5,360,016 | 11/1994 | Kovacevic ................... 128/782 |

FOREIGN PATENT DOCUMENTS

| 436121 | 7/1991 | European Pat. Off. . |
| 3030897 | 3/1982 | Germany . |
| 463127 | 10/1990 | Sweden . |

Primary Examiner—V. Millin
Assistant Examiner—Robert N. Wieland
Attorney, Agent, or Firm—Andrus, Sceales, Starke & Sawall

[57] ABSTRACT

The invention relates to a measuring instrument for detecting muscular activity (F) especially in the area of the hand. The measuring instrument (1) comprises an elongated connecting part (2), by which at least two points of the hand (6) moving with respect to one another are supported so that the movement of these points is transferred to the connecting part, a hand-securing means (12), and a measuring transducer (3, 13) secured to the connecting part for providing a signal dependent on the movement between the said points of the hand and preferably proportional to this movement, which signal can be transferred to the device (10) providing the measuring results. The connecting part (2) comprises two branches (4a and 4b) which together form an angle (5) and are connected to one another in an articulated (9) manner so that the angle (5) between the branches forms a plane (20) which remains at least approximately constant. The first branch (4a) is supported by one finger (7) and the second branch (4b) is supported by a part (8) of the hand with respect to which the said finger moves, in this case the forefinger. A force measuring transducer (3) is placed to measure the force respectively dominant between the branches.

22 Claims, 3 Drawing Sheets

MEASURING INSTRUMENT FOR DETECTING DEGREES OF RELAXATION

BACKGROUND OF THE INVENTION

The invention relates to a measuring instrument for detecting muscular activity in the area of the hands in particular, comprising generally an elongated connecting part, on which at least two points of the hand moving with respect to one another are supported, so that the movement of these points is transferred to the connecting part, and at least one measuring transducer attached to the connecting part. The transducer provides signals depending on the movement between the said points of the hand, and these signals can be transmitted to a device to provide observation results. The invention also relates to a method for detecting at least the detachment of the measuring instrument installed in place by using a device that fixes the instrument to the hand, as well as to the use of the measuring instrument to observe or measure functional responses of muscular activity caused by electric stimulation.

SUMMARY OF THE INVENTION

In most cases, when a patient is anesthetized, a certain degree of muscular relaxation of the patient is needed, which can be provided by using relaxants which attenuate the activity of the neuromuscular junctures. Because different levels of relaxation are required for different types of surgical operations and because the relaxants also have an intensive effect on the muscles of respiration, it is extremely important to be able to define the level of relaxation both during the operation and before detaching the patient from a respirator. It is known that the level of relaxation can be followed by electrically stimulating the nerve of a suitable muscle, for instance muscles of the hand, such as adductor pollicis, hypothenar eminence, and the first dorsal interosseous, and by measuring the size of the muscular activity response caused by it. In order to measure the response, i.e., the muscular contraction caused by the stimulation, different measuring instruments have been developed. In some situations, there is also a need to recognize or measure either intentional or unintentional unstimulated muscular activity.

One measuring method comprises measuring the electric response of the muscles by using electromyography (EMG) which, however, is a complex method requiring accuracy and as such is generally suitable for research and laboratory use. The use of an acceleration transducer attached to a finger has been suggested as another possibility. This measuring arrangement is easy to set in place but the arrangement is very sensitive to the quality of the pad of the finger as well as to unintentional displacements of the finger. Therefore, the reliability of this measuring arrangement is fairly questionable and the accuracy of measurement is probably only slightly better than what is achieved by visual monitoring.

Efforts have been made to eliminate this influence of the factors independent of the stimulation by using the arrangement described in publication DE-39 39 790, according to which the respective measuring transducers are placed both on the thumb and the little finger. The type of transducer is not disclosed but only an acceleration transducer is capable of providing a signal in the arrangement described. Consequently, the arrangement of the publication stimulates both the adductor pollicis muscle and the hypothenar eminence muscle simultaneously, and only responses obtained from both of them are accepted as measuring results. To a certain extent, this reduces the possibility of errors but does not eliminate them to the extent desirable in practice.

Publication U.S. Pat. No. 4,444,205 describes a strip-like measuring transducer made of conductive elastomer which is placed in the longitudinal direction along the thumb and around its tip. In this arrangement a deflection of the thumb causes a deformation of the elastomer and, consequently, a change in its resistance.

This type of measuring transducer measures the size of the thumb movement and transducers of this kind should comprise as low as possible deformation resistances so that the actual transducer will not limit muscular movement. This type of transducer is also fairly sensitive to changes in the thumb position caused by external factors, therefore, its reliability is not better than that of acceleration transducers.

Publications DE-34 44 628 and DEZ Anästhesie. Intensivtherapie. Notfallmedizin, Band 19, 1984, pp. 78–80; Friesdorf, Schultz, Mehrkens: "Eine einfache Methode zur Bestimmung und Registrierung des Relaxationsgrades" describe a measuring arrangement in which a steel strip, or correspondingly, a plastic strip is secured on the back of the hand, the strip extending on top of the thumb and the thumb being secured to the strip. Strain gauges are placed as the measuring transducer on the steel or plastic strip, providing a signal for a deflection of the strip caused by stimulated muscular activity of the thumb. Indeed, the arrangements according to these publications measure the force which is clearly less sensitive to external disturbances than the acceleration transducer arrangements. However, the two arrangements using strain gauges, as well as the motion size transducer described above, and the above-mentioned arrangements using acceleration transducers have the accuracy-decreasing disadvantage that no prestressing force focused on the thumb or on the little finger, respectively, are used but the thumb or the little finger are in a complete rest position without stimulation. In practice, this prestress cannot even be arranged in the arrangements according to these publications because, when trying to achieve this, the measuring instruments formed in the above-described ways do not stay in place, or no desired prestress is generated as the result of their design, or the prestress itself causes measuring errors.

The volume by Ehrenwerth Eisenkraft: ANESTHESIA EQUIPMENT, Principles and Applications, 1993, Chapter 15 "Neuromuscular Block Monitoring", describes an arrangement in which a desired prestressing force of 0.2–0.3N (200–300 g) is arranged on the thumb for optimizing the mutual orientation of the actin and myosin muscle fibers. In the arrangement described the whole arm as well as the palm of the hand are firmly secured in place and the thumb is pulled back by a screw arrangement. The response caused by the stimulation is measured by a pressure transducer the type and location of which is not shown. This kind of arrangement is large in size and difficult to use and, consequently, is mainly applicable to research and laboratory use. Furthermore, securing the patient's hand in a completely stationary position for the long period of time required by an operation may cause problems.

In addition to the problems described above, in the measuring instrument intended to be used for measuring, e.g., stimulated reactions of the thumb, the fact should be taken into account that the force being measured normally increases to value 5N (5 kg) and in extreme cases it can increase up to 10N (10 kg).

The object of the invention is thus to provide a measuring instrument which can be used to observe qualitatively and, when needed, to measure quantitatively intentional or unintentional movements of muscles and typically those of any finger, which movements may be stimulated or unstimulated. Another object of the invention is the kind of measuring instrument which can be used to focus on the finger a desired amount of prestressing force when needed. The purpose in particular is to provide on the finger an accurate-size and measured prestressing force against which the actual movement of the finger has to work. The third object of the invention is a type of measuring instrument which is small in size and quickly and easy to secure to the hand and does not require the hand or arm to be secured into a stationary position but allows a free position of the hand. Consequently, the use of the measuring instrument has to be so simple that it can be used in a routine-like manner. The fourth object of the invention is the kind of measuring instrument which provides an accurate measuring result, i.e., a signal which is as accurately as possible proportional to the real reaction force, i.e., the response of the finger; which is essentially independent of the position of the hand, the pad of the hand, and movements of the hand caused by other reasons, or changes thereof. The fifth object of the invention is a kind of measuring instrument providing a signal, or providing a signal on the basis of which one can unambiguously observe the detachment of the measuring instrument from the hand. The sixth object of the invention is a measuring instrument adapted, or adaptable in a simple way, to be applied to different types of hands.

The disadvantages described above can be eliminated and the above-defined objectives implemented by the measuring instrument according to the invention which is characterized in what is defined in the characterizing part of claim 1, and by the method according to the invention which is characterized in what is defined in the characterizing part of claim 10, and by the use of the measuring instrument according to the invention which is characterized in what is defined by the characterizing part of claim 15.

An essential advantage of the invention is that the measuring instrument and method according to the invention can be used to exert on the thumb or other finger an accurate prestressing force of the desired size although the instrument is small and easy to use. Another essential advantage of the invention is that the measuring result is accurate and very linear starting from a zero value of the response force of the thumb and extending up to high response force values, yet other movements of the hand or a change in its position or other environmental factors do not have a significant influence on the accuracy and reliability of the measurement. Yet another advantage of the invention is that the measuring instrument according to it is simple and firm and, therefore, does not break easily and that by using it, the most advantageous finger regarding the respective use can be selected for the recognition and measuring of the finger movement.

BRIEF DESCRIPTION OF THE DRAWINGS

The invention is described in the following in detail with reference to the appended drawings.

DETAILED DESCRIPTION OF THE PREFERRED EMBODIMENT

The same reference numbers are used in the following description for the same and corresponding components of the measuring instrument in different embodiments of the measuring instrument.

Figure 1:
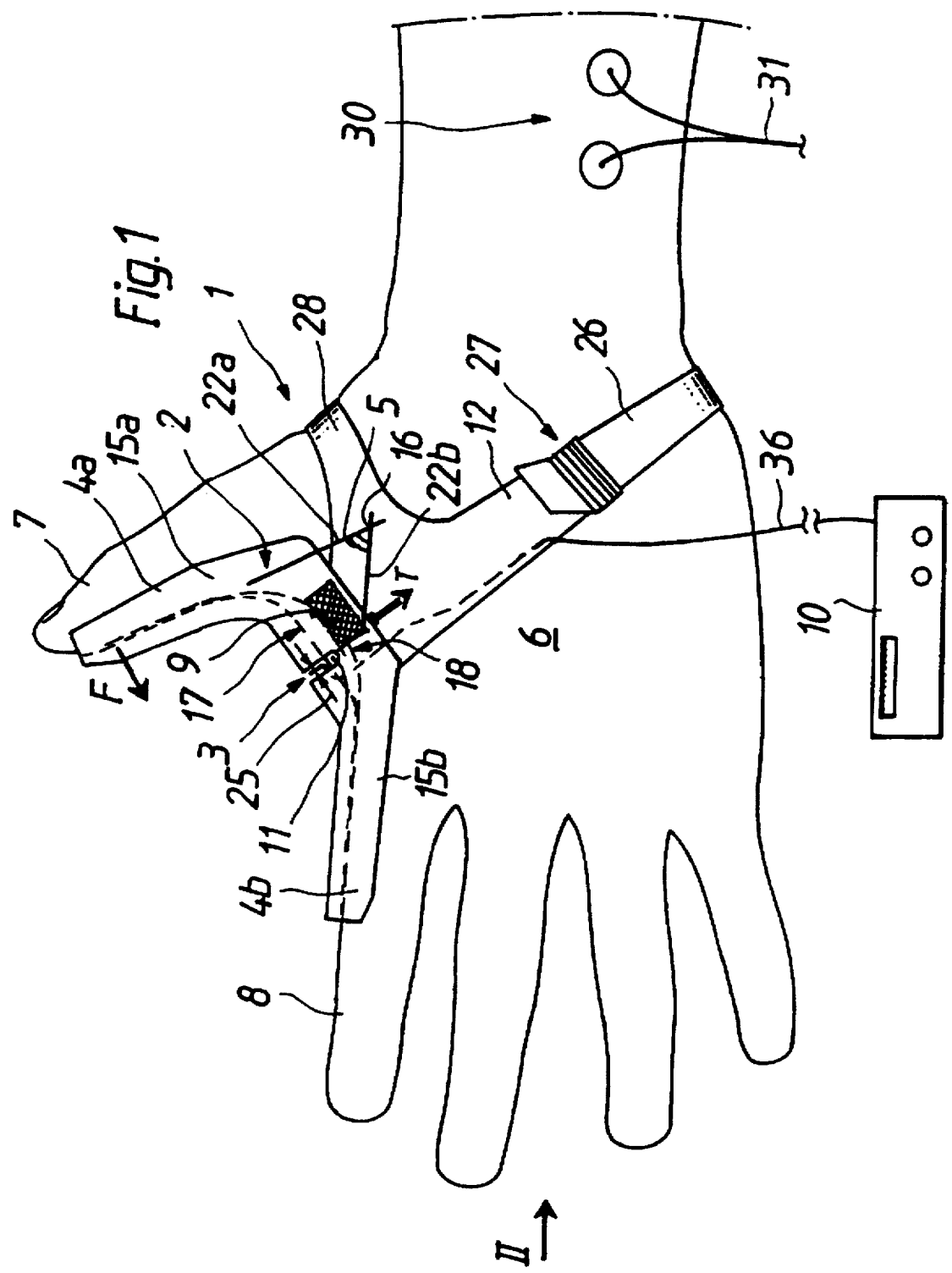
FIG. 1 represents one embodiment of the measuring instrument according to the invention, in which the finger that primarily moves is the thumb, as secured to the hand on the back of the hand from direction I of FIG. 2.
Figure 2:
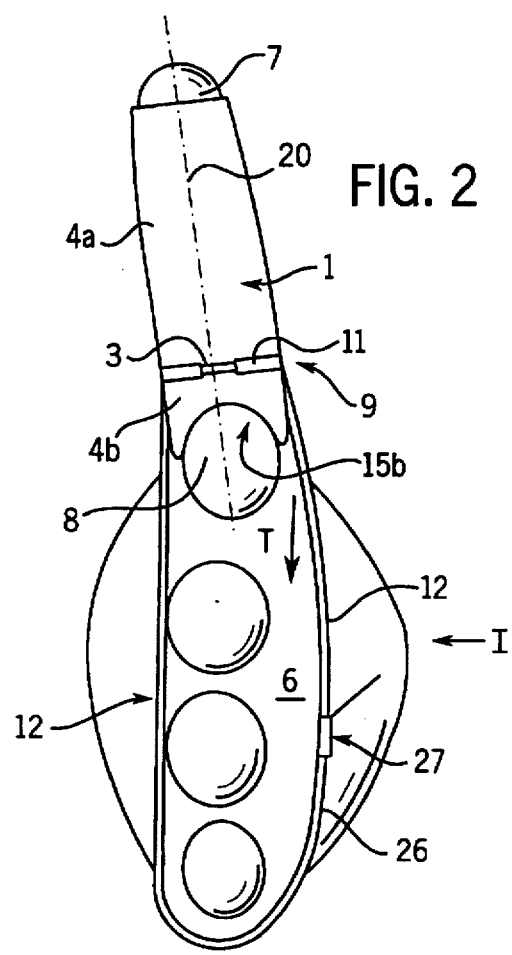
FIG. 2 presents the arrangement according to FIG. 1 in the direction of the fingers and in direction II of FIG. 1.

FIGS. 1 and 2 present the measuring instrument according to the invention as located in place in the area of hand 6. The hand in this context refers to the area extending from the wrist to the finger tips, including the wrist, and the palm of the hand refers to the area of the hand which comprises no fingers. Measuring instrument 1 according to the invention generally consists of an elongated connecting part 2 comprising two branches 4a and 4b which together form angle 5 whose size can vary considerably in the different embodiments. In this embodiment these branches 4a and 4b comprise the connecting part 2 of a V-shape or an L-shape. This connecting part 2 is placed in hand 6 so that thumb 7 is supported by first branch 4a and forefinger 8 is supported by second branch 4b, whereby, consequently, plane 20 of angle 5 between the branches sets approximately in the direction of the hand and the connecting part is between the thumb and the forefinger. It is appropriate to shape branches 4a and 4b of this connecting part 2 into the form of troughs the concave sides 15a and 15b of which point away from angle 5 between them, whereby concave side 15a of first branch 4a comes against thumb 7 and concave side 15b of second branch 4b comes against forefinger 8. In this case, the connecting part remains well in place in the hand and the fingers are not apt to move.

First branch 4a and second branch 4b of connecting part 2 are connected to one another by articulation 9 so that the branches are allowed to at least slightly move on the plane of angle 5 between them, i.e. on movement plane 20 towards one another when force F twisting thumb 7 is effecting on the thumb, the force being caused by, e.g., a contraction of the adductor pollicis muscle caused by stimulation, i.e., by the response of muscular activity to the stimulation. In the embodiment of FIGS. 1 and 2, this articulation 9 comprises the flexibility of the area joining branches 4a and 4b. The actual branches 4a and 4b are preferably of as stiff a material as possible in order to transfer force F exerted by the thumb as effectively as possible to the measuring transducer 3 or 13 described below. As already stated earlier, area 9 joining the branches is slightly flexible or bendable, whereby it provides in practice a structure functioning in the way of an articulation comprising a virtual articulated shaft which is approximately perpendicular to the image plane, although no actual mechanical articulation point is perceivable. This area of articulation 9 is marked in FIG. 1 approximately with cross-ruling but the area has no precise boundaries and the extent of the area depends on the more detailed shaping of connecting part 2 and on the quality of the material. However, it is essential that force F may cause a small change in angle 5 because of the flexibility of the area of articulation 9. It is essential that the structure of articulation 9 is comprised so that the above-described plane 20 remains at least approximately constant while force F of the muscle effects branches 4a and 4b of the connecting part, i.e., the branches move towards one another and away from one another on this motion plane 20 regardless of the size of angle 5, per se. This ensures good accuracy of measuring. The motion plane 20 formed by angle 5 is approximately in the direction of the image plane in FIGS. 1, 3–4, 5B, and 6.

Figure 3:
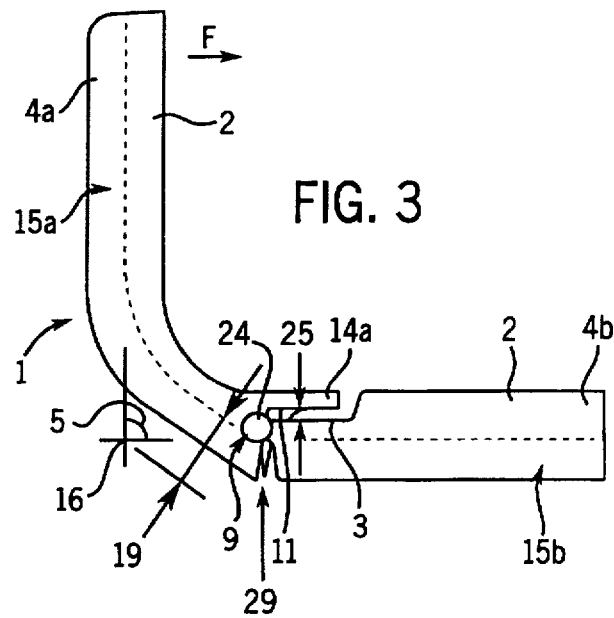
FIG. 3 represents the second embodiment of the measuring instrument according to the invention as a separate unit in the same illustration as in FIG. 1.
Figure 4:
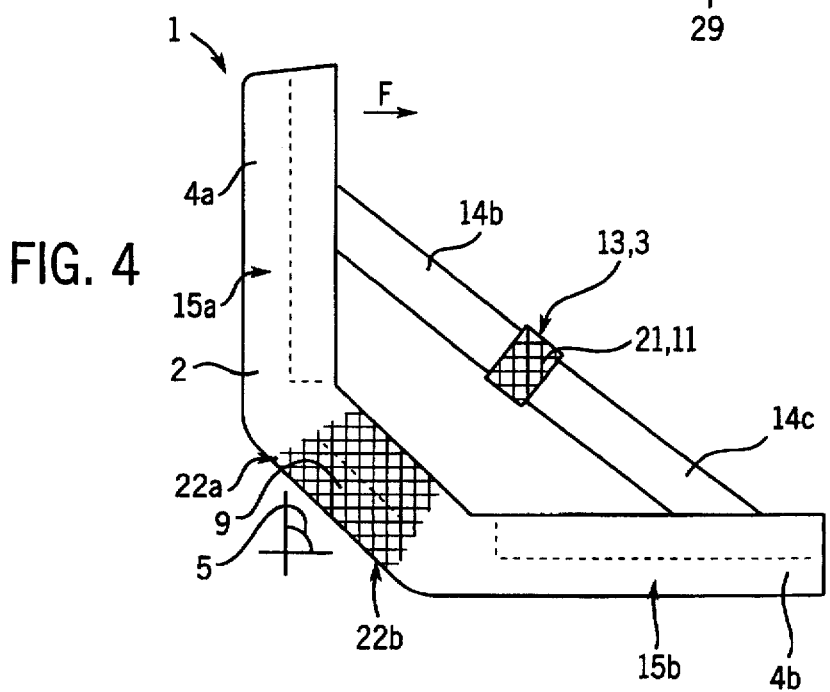
FIG. 4 presents the third embodiment of the measuring instrument according to the invention as a separate unit in the same illustration as in FIG. 1.

FIG. 4 presents another embodiment of the connecting part 2 according to the invention, comprising the area of articulation 9 corresponding to the above-described one which is similarly marked approximately with cross-ruling and comprises a larger area on the plane of angle 5 than that in the embodiment of FIG. 1, and a virtual articulation shaft which is approximately perpendicular to the image plane. In contrast, the embodiment of FIG. 3 presents the articulation structure 9 provided with a shaft 24. Naturally, according to FIG. 3 it can be understood that branches 4a and 4b can turn with respect to one another on the plane of angle 5, which is the same as the image plane, around shaft 24 which is perpendicular to the image plane and the plane of angle 5. It is obvious that other types of articulation structures can be used but it is advantageous to use articulations 9 which only allow the movement of branches 4a and 4b generally on the plane of angle 5 or on some other corresponding motion plane 20, whereby a physical, fixed articulation shaft line is illustrated in the connecting part, or a virtual fixed articulation shaft line is illustrated. The measuring instruments presented in FIGS. 3 and 4 are intended to be placed between the thumb and the forefinger in a similar way as the measuring instrument according to FIGS. 1 and 2. All the same types of articulation structures can be used in the measuring instruments of FIGS. 5A, 5B and 6 as what is presented in connection with the other figures, although they are intended to be placed between the middle finger and the palm of the hand and, correspondingly, between the forefinger and the middle finger.

Connecting part 2 according to FIGS. 1 and 2 comprises, for placing the measuring transducer 3 which measures force F exerted by thumb 7, a narrow slot 11 between branches 4a and 4b and in portion 17 connecting the branches, extending towards the area of articulation 9 from the spread angle, i.e., the open area between the branches. Height 25 of slot 11 in the direction of the tangent of the circumference corresponding to angle 5 is so small that it preferably allows as small a change as possible in angle 5, as the first and the second branch are pressed towards one another by using maximum force F, such as a force of 10N. If for any reason a fairly large change in angle 5 has to be allowed, it is possible, although the accuracy of the measurement slightly decreases. We do not know if values examined accurately enough exist below which the change in angle 5 should be in order to achieve the desired accuracy, but there is reason to assume that a change as small as possible in the angle improves the accuracy for two reasons. The first reason is that the elastic constant of the articulation structure does not need to remain constant during the travel of change of the angle. The second reason is that the force caused by a certain size movement of the finger, which would change if angle 5 changes, cannot do this. Height 25 of slot 11 in this case is adjusted to be close to the thickness of transducer 3 in the direction of the transducer in which it measures the force. As this transducer 3 measuring the compression force is placed in slot 11 in the position where its direction of dynamometry is joined with the height of the slot, it is understandable that force F exerted by the muscular activity of the thumb provides a slight decrease in angle 5 caused by articulation 9 and, correspondingly, a decrease in the height measure 25 of slot 11, whereby the compression force is exerted on measuring transducer 3. Measuring transducer 3 provides a signal of this mutual compression force F of the branches which is transmitted along line 36 to device 10 providing a measuring value. The transmission of the signal, obtained from measuring transducer 3, along line 36 and the further processing thereof in device 10 to provide a measuring value or, when needed, an observation result, comprises prior art known per se, therefore, it is not described further in this application. Slot 11 extends in a direction perpendicular to plane 20 of angle 5 of connecting part 2 along the whole width of connecting part 2, as can be seen in FIG. 2, and the direction of the depth perpendicular to slot 11 and the height and width thereof is preferably in the direction of either branch 4a or 4b or in the direction of any line between the two. The direction of depth of slot 11 is thus set between the directions of lines 22a and 22b limiting the angle 5 in this embodiment.

Figure 5A:
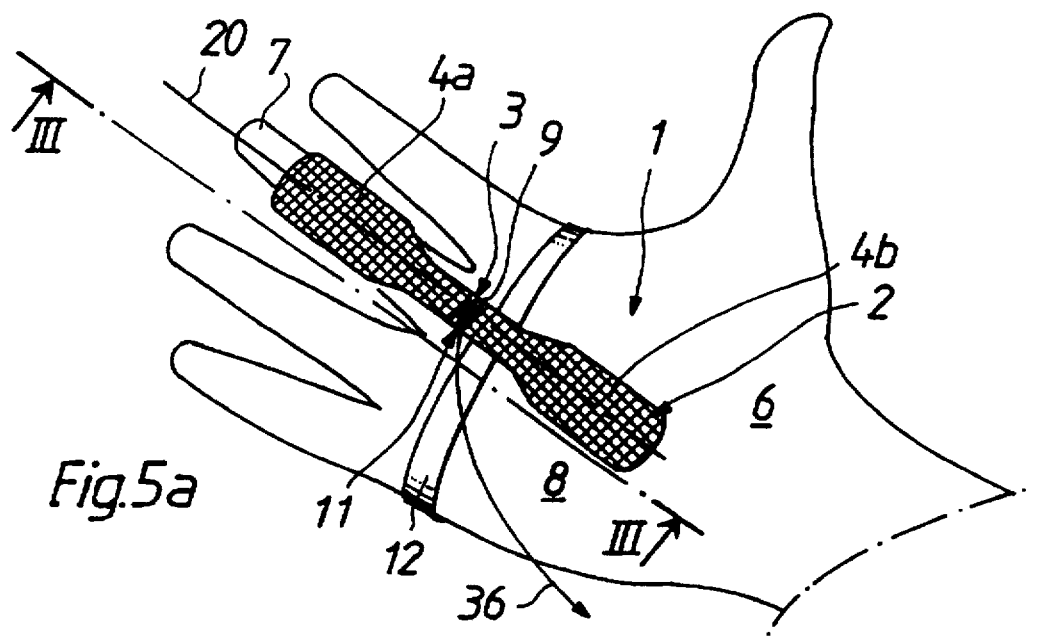
FIG. 5A presents the fourth embodiment of the measuring instrument according to the invention, in which the middle finger is the primarily moving finger, as secured to the hand on the gripping side of the hand in direction IV of FIG. 5B.
Figure 5B:
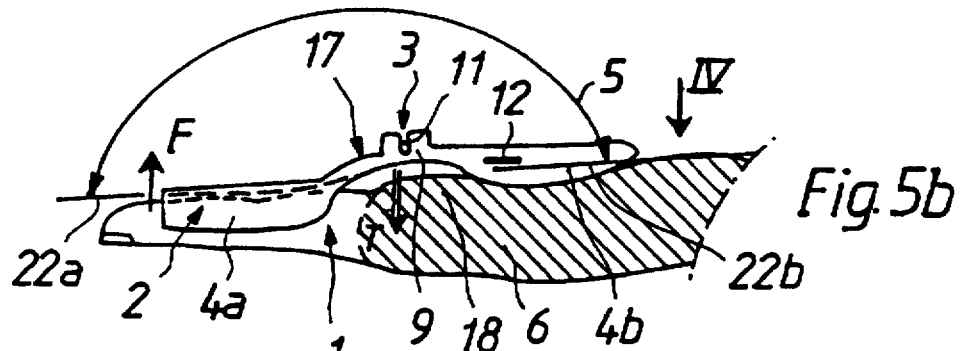
FIG. 5B presents the arrangement according to FIG. 5A as a cross-section along plane III—III of FIG. 5A.
Figure 6:
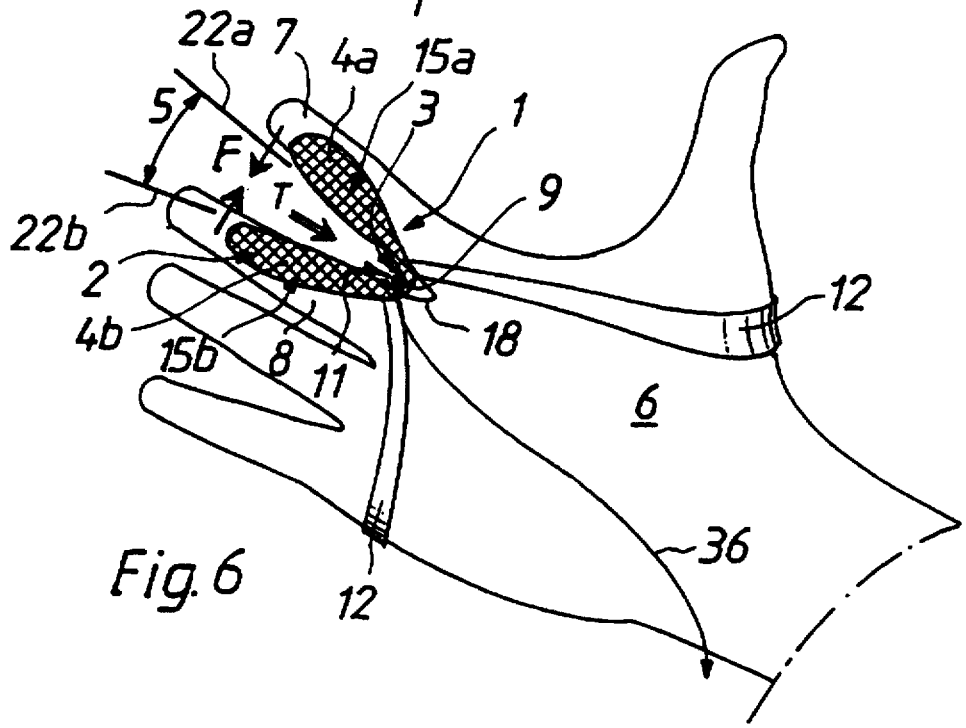
FIG. 6 presents the fifth embodiment of the measuring instrument according to the invention, in which the moving fingers are the forefinger and the middle finger, as secured to the hand as viewed from the back of the hand.

The embodiments of FIGS. 5A, 5B and 6 apply the above-described arrangement for exerting force F of the finger to measuring transducer 3 by using the small slot 11 between branches 4a and 4b, the measuring transducer in question being placed in the slot. Only the design and dimensioning of the parts deviate from one another. Regarding these embodiments, any of the arrangements described below may also be applied for exerting the force on the transducer as well as any type of measuring transducer described in this application.

In the embodiment of FIG. 3 a corresponding small slot 11 is provided between projection 14a of first branch 4a and second branch 4b, whereby height 25 of the slot is approximately perpendicular to the length of second branch 4b and the depth of slot 11 is approximately in the direction of second branch 4b, unlike in the embodiment described above. It is obvious that in this kind of embodiment slot 11 can also be directed in many other directions so the invention is by no means limited to the above-described locations or positions of slot 11, as long as height 25 of the slot corresponds to the thickness of measuring transducer 3.

FIG. 4 illustrates another embodiment in which branches 4a and 4b of connecting part 2 are joined at the outer ends thereof by projections 14b and 14c which are placed one after another and approximately in the direction of the tangent of the circular curve corresponding to angle 5 between the branches. Slot 11 can be arranged between these projections 14a and 14b, the height 25 of the slot being preferably in the direction of projections 14b and 14c. Alternatively, in the embodiment of FIG. 4, a small flexible portion 21 can also be arranged between projections 14b and 14c, allowing a change as small as possible for angle 5 between the branches when the thumb influences the connecting part by force F. In this case, instead, another kind of measuring transducer 13 is used or this flexible area 21 in itself provides transducer 13 measuring its deformation, the transducer being described below. In this embodiment is also true what is described above about the allowed change in the angle and its influence on the accuracy of measurement. The solution of FIG. 4 can also be applied to the measuring instrument and the connecting part described in the other figures, especially in FIGS. 5A–5B and 6. The flexible area 21 can be at an essential distance from the area of articulation 9 or it can be very close to it. The distance can be, e.g., over 5 mm, over 10 mm, or over 25 mm, or it can be so small that flexible area 21 is placed inside the area of ariculation 9 close to the virtual articulation line or against it. This flexible area 21 generally used for measuring the force cannot be against the real or virtual articulation shafts when the measuring of the compression caused by the fingers is based on the recognition of a shearing force or a compression force. Only transducers, such as certain types of piezoelectric transducers, suitable for recognizing the twist caused by the compression force of the fingers, can be placed on the real or the virtual articulation shaft line.

The general features of measuring instrument 1 according to the invention are described above. The measuring instrument according to the invention especially also comprises hand-securing means 12 consisting of, e.g., first strap 26 connected to portion 17 which joins together branches 4a and 4b of connecting part 2, the strap traveling around the palm of the hand starting from the connecting part, then close to the wrist and over the back of the hand back to the connecting part, as can be seen in FIGS. 1 and 2. The first portion 26 also comprises a tensioning member 27 which can be of any known type enabling the tensioning of strap 26 and locking the same in a desired point either completely steplessly or almost steplessly. Different belt clips or clamps 27 of this kind are known and used in different connections so it is not described in more detail in this description. In addition to this, it is preferable to provide the hand-securing means with another branch 28 which goes around thumb 7, as can be seen in FIG. 1. This second branch 28 is not quite necessary but it makes securing of measuring instrument 1 to hand 6 more precise and reliable. Other types of hand-securing means can also be used as long as they are reliable enough to maintain the desired prestressing force. It is obvious that measuring instruments according to different embodiments used in connection with different fingers and/ or the palm of the hand require the use of at least somewhat different hand-securing means.

According to the invention angle 5 between branches 4a and 4b of the connecting part is made large enough so that when connecting part 2 of the measuring instrument is pulled by using the above-described hand-securing means 12 and its first strap 26 and clamp 27 between thumb 7 and forefinger 8 in direction T shown in the figures, whereby connecting part 2 projects towards the crotch of the thumb 18 (or correspondingly, towards area 18 between the middle finger and the palm of the hand or crotch 18 between the forefinger and the middle finger). Then first branch 4a is compressed against thumb 7 and second branch 4b is compressed against forefinger 8, twisting them away from one another and away from the rest position. In this way, by actually twisting thumb 7 away from the rest position with respect to forefinger 8, thumb 7 causes a prestressing force as a reaction which is parallel to the measured force F exerted by the thumb. This prestressing force can be perceived by simply following device 10 providing the measuring result, when setting the measuring instrument in place, and by tensioning first strap 26 by a clamp 27 until the device can be seen to indicate a low prestressing force the size of which can be the 0.2–0.3N described above. Upon perceiving that the prestressing force has been achieved, tensioning strap 26 is stopped and the measuring instrument and especially its connecting part 2 are left in the hand in this state, i.e., in a state in which this predetermined prestressing force is dominant between the fingers while the muscle(s) to be observed are inactive. In this way, the desired prestressing force and optimizing the mutual orientation of the muscle fibers of the muscles of the thumb have simply been achieved. It is obvious that in this way the measuring instrument according to the invention can be used to set any prestressing force of a desired size. If branches 4a and 4b of the connecting part are supported by other parts of hand 6 than the thumb and the forefinger, the angle between the branches must be chosen differently in the manner described below and the measuring instrument must be tensioned, by using the hand-securing means, towards the area between these supporting points of the hand. For instance, when using the forefinger and the palm of the hand as the supporting points of the branches of the connecting part, as in the embodiment of FIGS. 5A, 5B, clamping in place is effected towards root 18 of the middle finger. The measuring instrument and the connecting part are thus placed on the side of the hand in whose direction the forces of the palm of the hand and/or the finger(s) act on while working, and the measuring instrument is pushed against these forces of the hand to provide the precompression force. The above-described is possible because a transducer which measures the force is used, whereby the static forces caused by the fingers and/or the palm of the hand are also perceivable.

In addition, this particular pretensioning or some other pretensioning, any value different from zero being sufficient as the size thereof, can be used to perceive a detachment of the measuring instrument from the hand. When using some prestressing force, this particular prestressing force obtained by strap 26 and clamp 27 is set as the new zero point of the actual measuring which is used to measure the response of stimulated muscular activity. If at any stage of the measuring in which the muscle of the thumb is not stimulated, the measured value is negative, this naturally indicates that the measuring instrument has either loosened or been completely detached. Therefore, device 10 that provides the measured value can be provided with a special alarm system which gives an alarm when the signal provided by measuring transducer 3, 13 becomes lower than some of the limit compression forces appropriately detected and determined in advance. This limit compression force can be determined to be the same as the prestressing force, whereby an alarm follows immediately when the measured value drops to zero. Generally, it is perhaps practical to define the limit compression force to be slightly lower, whereby an alarm is provided when the measured value decreases to a corresponding, slightly negative value. In any case, the medical staff is able to correct the securing of the measuring instrument in the hand of a patient on the basis of this indication, and there is no possibility to draw the wrong conclusions as is possible in all solutions of the prior art.

The angle between thumb 7 and forefinger 8 in hand 6, when the fingers are moved voluntarily and normally away from one another, is typically in the order of 90° or slightly smaller. However, there are essential differences in human hands in this area. Angle 5 between branches 4a and 4b of the connecting part of measuring instrument 1 should be slightly larger than the angle between thumb 7 and forefinger 8 in the voluntary movement thereof mentioned above. In this way, when angle 5 between the branches is slightly larger than the angle naturally taken by the thumb and the forefinger, the thumb and the forefinger can be forced out of the rest position by using the above-mentioned tensioning of strap 26 and the prestressing force is given to measuring transducer 3 or 13. Typically, angle 5 between branches 4a and 4b of the connecting part is thus in the order of 70°–120° but in special cases there might be a need to use larger or even smaller angles in connecting parts 2. The possible limit values of the angle are also 80° and 110° in proportion to either one another or to either one of those mentioned above.

If the measuring instrument according to the invention is an embodiment in which the parts of the hand that move with respect to one another are some other fingers than those described above, or the palm of the hand or any point or area in the palm of the hand, the size of angle 5 must naturally be selected correspondingly.

The first 4a of the branches of connecting part 2 of measuring instrument 1 can be supported, in addition to the thumb in the manner described above, also by any other finger and the second 4b of the branches of the connecting part can, correspondingly, be supported by the palm of the hand or some other finger. The palm of the hand here refers to the entire part of hand 6 which is located between the fingers and the wrist. For instance, if first branch 4a is supported by middle finger 7 and second branch 4b by the palm of the hand 8, as seen in FIGS. 5A–5B, the value of angle 5 will be in the order of 180° or slightly larger, such as 200°, and possibly even up to 220° as well as approximately between 170°–210°. In contrast, if first branch 4a is supported by forefinger 7 and second branch 4b by middle finger 8, as seen in FIG. 6, the value of angle 5 will be approximately in the order of 20°–70°. The possible limit values of the angle are about 30° and, correspondingly, the upper limit is 50°–60°, such as 55°, as combined either with one another or with either one of the former. Due to the differences in hands, accurate values of the angle are difficult to provide. Depending on the angle, motion plane 20 should remain approximately constant with the aid of the articulation structure 9 because the relative movement of the points of the hand independent of the environment can then be measured when the measuring transducer of the force is used according to the invention. However, on the basis of the tests performed, it is believed that the measurement between the thumb and the forefinger, and possibly the measurement between the middle finger and the palm of the hand is advantageous and in this way, at least one finger is forced out of the rest position in the desired way. The advantageousness of different measured fingers and the directions of movement of the fingers are influenced, in addition to which muscular movement one wishes to study, also by the possibilities of preloading the muscles in question and when needed, the possibilities for stimulation.

Particularly, according to the invention the connecting parts, or rather the measuring instruments 1 can be manufactured, and instruments with angles 5 of different sizes between the branches can be kept in the storage of the place of use, such as a hospital, and from them one can select the one that best fits the hand of a patient. Patient's hands can be of different sizes, as is the case with child patients at least, so there can be connecting parts of different sizes at hand.

The embodiments of connecting part 2 according to FIGS. 1–3 and 5A–6 use compression force transducer 3 which is preferably comprised of a thick film resistance transducer of polymer, such as a transducer called FSR (Force Sensing Resistor™) which is a trademark registered by a company called "Interlink Elektronics". Another alternative uses a piezo-resistive compression transducer, a capacitive compression transducer or the like. Typically, these compression force transducers 3 are micromechanical transducers but, in principle, any sufficiently small transducer known per se which operates on a suitable range of force can be used. It is preferable to use such measuring transducers 3 which provide a signal proportional to force F also in a static state of loading, which is generally the case with respect to these transducers. In the embodiment of FIG. 4 in which the flexible portion 21 is between projections 14b and 14c, any shearing force transducer, a piezoelectric transducer, inductive pick-off or the like can be used. However, some of these transducers have the disadvantage that they provide a signal only in a dynamic state. The use of such transducers is more troublesome. However, types of measuring transducers 13 exist which are capable of providing a signal proportional to a force F also under a static load F. Because these measuring transducers 3, 13 are known per se and generally available commercially, they are not described here in more detail. If the measuring instrument is intended to be used only to recognize qualitatively some movement of the finger, almost any type of force measuring transducer can be used. In contrast, if the intention is to measure quantitatively the force caused by the movement of the finger, the type of transducer should be carefully chosen taking into account the design and requirements for accuracy of the measuring instrument.

The definitions 'compression force', 'precompression force', and 'threshold compression force' are used above in this application, concerning the forces to be measured, but it is obvious that in another kind of embodiment of the invention the force measuring transducer can be used to measure and/or observe tractive forces, pretractive forces, and threshold tractive forces or, alternatively, bending forces, prebending forces, threshold bending forces, or torsional forces, pretorsional forces and threshold torsional forces. The alternative used in each measuring instrument 1 according to the invention depends on the structure of the measuring instrument which can vary considerably within the scope of the invention. However, as there are directions of movement in the hand which inherently result in a compression, e.g., when clenching the fist, it is believed that the measurement of the compression forces leads to simpler measuring instruments. Of course, nothing prevents one from converting the directions of movement of the hand from connecting part 2 into a tractive force which influences a suitable member of the measuring instrument, or into a tensile stress or other forces and stresses described above. Force measurement transducer(s) 3, 13 have to be selected and placed correspondingly. Generally, the terms 'force', 'preforce' and 'threshold force' are used for these.

In order to prevent the penetration of connecting part 2 into the crotch 18 of the thumb (or, correspondingly, into area 18 between the middle finger and the palm of the hand, or into crotch 18 between the forefinger and the middle finger), disturbing the transfer of force F from thumb 7 to measuring transducer 3, 13, the portion 17 which joins branches 4a and 4b, and especially the bottom of the connecting portion pointing towards crotch 18 of the thumb have to be at distance 19 from intersection 16 of longitudinal lines 22a and 22b, respectively, of the branches and towards the direction of the opening of angle 5 between branches 4a and 4b. Thus a truncated V-shape is provided for the connecting part, in which the support, i.e., connecting portion 17 which joins branches 4a and 4b, forms a shape which truncates the form, as can be clearly seen in the figures. It is also possible to shape the connecting part so that the concave parts 15a and 15b are only along the length of the actual branches 4a and 4b, whereby the connecting portion 17 comprises no bottom but only sides approximately in the direction of the plane of angle 5, as shown in FIG. 4. It is essential in this design of connecting part 2 that the connecting part is not essentially supported by other points of the hand but the inner surfaces between the thumb and the forefinger, and only the hand-securing means 12 is compressed against the other parts of the hand. This connecting portion 17 typically contains articulation 9 in the form of either an articulation area or a shaft. If branches 4a, 4b of the connecting part are supported on other parts of hand 6 than the thumb and the forefinger, the portion joining the branches has to be shaped so that it does not press area 18 between the said supporting points of the hand, as clearly shown in FIGS. 5B and 6. For instance, when using the middle finger and the palm of the hand, it is preferable to shape the portion 17 joining the branches into a curved shape away from hand 6 so that root 18 of the middle finger does not compress the measuring instrument but is allowed to deform in a natural way.

Because several measuring transducers 3 or 13 have the disadvantage that they are not completely linear from the zero value of the force exerted on them, but only from some transducer-specified basic load or basic force, such a basic load can be arranged in all the above-described arrangements in a simple way. In the embodiments of FIGS. 1-2, 4, 5A-5B and 6, the connecting part is shaped so that height 25 of slot 11, when the connecting part is in a free state with the measuring transducer removed, is slightly smaller than the thickness of transducer 3 in the same direction. When this measuring transducer is placed in place in the slot, branches 4a and 4b must be turned slightly away from one another for the transducer to be placed between, and when the branches are released, the flexibility of articulation area 9 causes the desired basic load to be exerted on the measuring transducer. In the embodiment of FIG. 3, this basic load can be exerted on the transducer by using, e.g., a spring 29 arranged between branches 4a and 4b which is placed so that it presses the height of slot 11 into a smaller size, therefore, the spring is placed on the other side of shaft 24 than slot 11. In the embodiment of FIG. 4, correspondingly, the flexibility of articulation area 9 can be used to provide a basic load between projections 14b and 14c which is focused on transducer 3 or 13, respectively. Generally, the basic load is smaller than the precompression force described above. However, it is further possible to combine the above-described provision of the precompression force with the provision of the basic load, whereby both can be provided simultaneously by the tensioning procedure carried out by using the hand-securing means. It is obvious that these provisions can also be kept apart from one another.

The stimulation of the muscle of the thumb or some other finger selected for the measurement is effected by using any method known per se, or which will be known, which takes into account the voltage of electric pulses, the shape of the pulse, the number of the pulses, etc. The stimulation is focused on the nerve in question by, e.g., using electrodes 30 in a manner known per se, which receive their electric pulses along lines 31. Because the technique of the stimulation is already known and the invention is not actually related to it, it is not described in this application in more detail.

It is obvious that in addition to the above-described arrangements which use one transducer 3, 13, the scope of the invention can comprise the use of embodiments comprising several measuring transducers. The transducers can be mutually identical or they can function on the same principle but be of different types (e.g., designed for different size forces), or they can function on different principles. Similarly, the measuring instrument can be designed to measure with respect to one another, e.g., the movement of three or more points moving with respect to one another, whereby typically several transducers of preferably the same type are used. The compression force between the fingers, or between the palm of the hand and the finger, which is to be measured, i.e., the mutual compression forces of the finger(s) and/or the palm of the hand acting towards one another are measured, according to the invention, essentially in the motion plane 20 of angle 5 in the direction of any tangent of the curve of angle 5, as described above, because the compression force generally acts in this particular direction.

We claim:

1. A measuring instrument adapted for detecting muscular movement activity in the area of the hand, the measuring instrument (1) comprising:

a generally elongated connecting part (2), by which at least two points of a hand moving with respect to one another are supported so that the movement of these points is transferred to the connecting part, the connecting part having at least two branches (4a,4b) with form an angle (5) theebetween, the two branches being joined with each other at an articulation point (9) in such a way that the angle (5) forms an approximately constant motion plane (20) for the branches, the first branch being supported by a first finger (7) and the second branch (4b) being supported by a second finger (8) with respect to which the first finger moves, and at least one force measuring transducer (3,13) secured to the connecting part, the force measuring transducer providing a signal dependent on the movement between the points of the hand, the signal being transmitted to a device (10) providing observation results, the force measuring transducer (3,13) placed to measure a compression force (F) between the branches predominant on the side of the branches whereto their mutal forces are pointed.

2. The measuring instrument according to claim 1, wherein the second branch (4b) is supported by the palm of the hand (6).

3. The measuring instrument according to claim 1, wherein a slot (11), which is small compared to the distance between the branches, is provided between the branches (4a,4b), the slot allowing as small a change as possible to the angle (5) between the branches by the influence of the muscular activity (F), and a compression force transducer (3) in this slot for measuring said compression force between the branches.

4. The measuring instrument according to claim 1, wherein the angle (5) between the branches (4a,4b) of the connecting part is preselected to be between 70°–120° so that the tensioning of the measuring instrument (1) by using a hand securing means (12) toward the area (18) of the hand between the first finger (7) and a second hand supporting point (8) turns the first finger away from a rest position, causing a pre-force on the measuring transducer (3,13).

5. The measuring instrument according to claim 1, wherein the angle (5) between the branches (4a,4b) of the connecting part is preselected to be between 170°–220° so that the tensioning of the measuring instrument (1) by using a hand securing means (12) toward the area (18) of the hand between the first finger (7) and a second hand supporting point (8) turns the first finger away from a rest position, causing a pre-force on the measuring transducer (3, 13).

6. The measuring instrument according to claim 1, wherein the angle (5) between the branches (4a,4b) of the connecting part is preselected to be between 20°–70° so that the tensioning of the measuring instrument (1) by using a hand securing means (12) toward the area (18) of the hand between the first finger (7) and a second hand supporting point (8) turns the first finger away from a rest position, causing a pre-force on the measuring transducer (3,13).

7. The measuring instrument according to claim 3, wherein the force measuring transducer (3) is one of a thick film transducer of polymer, a piezoresistive compression transducer, a capacitive compression transducer, and a micromechanical compression force transducer for obtaining a signal proportional to the movement of said points of the hand.

8. The measuring instrument according to claim 1, wherein the branches (4a,4b) of the connecting part are shaped like troughs, the branches having concave (15a,15b) sides which point away from said angle (5) between them, the point of articulation (9) connecting the branches being placed at a distance (19) from the intersection (16) of the longitudinal lines (22a,22b) of the branches towards said branches (4a,4b), providing a truncated (17) V-shape for the connecting part, whereby the branches of the connecting part are preferably supported by the thumb and the forefinger, and the crotch (18) of the thumb or a corresponding area between the fingers does not compress the connecting part, and that said articulation point (9) consists of an articulation structure provided with a pivoted shaft.

9. The measuring instrument according to claim 8 wherein the articulation point (9) consists of the flexibility of the material connecting the branches.

10. The measuring instrument according to claim 1, wherein a small flexible portion (21) is provided between the branches (4a,4b) of the connecting part, the flexible portion (21) allowing as small a change as possible for the angle (5) between the branches by the influence of the muscular activity (F), the flexible portion including a transducer (13) for measuring its deformation or, alternately, this flexible portion forms a transducer (13) measuring its own deformation, whereby the compression force between the branches is measured on that side of the branches whereto their mutual forces point.

11. The measuring instrument according to claim 10 wherein the transducer (13) measuring the deformation is one of a shearing force transducer, a piezoelectric transducer, and an inductive pick-off, the transducer obtaining a signal proportional to the movement of said points of the hand.

12. The measuring instrument according to claim 1 wherein the articulation point (9) of the connecting part (2) is flexible either through the influence of the structural substance of the area of articulation (9), or through the influence of a spring (29) installed in the connection with the articulation point, and the measuring transducer (3 or 13) is slightly oversize compared to the height of the point (11,21) reserved for it in the connecting part so that after the measuring transducer (3,13) has been set in place, a basic force is exerted on it which is essentially lower than the muscular forces (F) to be observed, and which is set at the new zero point of the measuring scale for making the measurement linear from this zero point onwards.

13. The measuring instrument according to claim 1 wherein the articulation point (9) of the connecting part consists of one of a flexible material of a connection portion (17) comprising the area of articulation and a shaft (24) joining the first and the second branches (4a,4b) to one another and is perpendicular to the plane (20) of the angle between them.

14. A method of detecting muscular activity (F) in an area of a hand of a patient, the method comprising the steps of:
providing a measuring instrument having a generally elongated connecting part having a first branch (4a) and a second branch (4b), the branches being joined with each other at an articulation point (9) and forming a motion plane (20) and an angle (5) therebetween;
supporting a first finger by the first branch of the connecting part;
supporting a second finger by the second branch of the connecting part, the first finger moving with respect to the second finger, said movement being transferred to the connecting part, the angle between the branches being larger than a natural angle between the first and second fingers;
fixing the measuring instrument to the hand with a hand securing means (12) such that said branches are tensioned by moving the hand securing means toward a hand area between the first finger and the second finger, the branches turning at least the first finger away from its rest position;
securing at least one measuring transducer (3,13) to the connecting part of the measuring instrument, the transducer being responsive to movement between the first and second fingers;
tensioning of the branches causes a reactive force (F) on the measuring transducer to measure the movement induced compression force existing between the branches, the tensioning being stopped and held upon achieving a predetermined magnitude of force;
providing a signal dependent on the movement between the points of the hand; and
transmitting the signal from the measuring transducer to a device for providing visually perceptible results.

15. The method according to claim 14 wherein when determining the magnitude of the force, the type of measuring transducer (3 or 13) used is taken into account so that, by using the force, the measuring is set to be as linear as possible.

16. The method according to claim 14 further comprising the step of selecting the size of the measuring instrument such that when the measuring instrument is placed in the hand (6) of each individual patient, the angle (5) between the branches is larger than the angle between the thumb (7) and the forefinger (8) of the patient without essential tension of the muscles.

17. The method according to claim 14 wherein the device (10) providing the observation result is a device which provides a result proportional to the force (F) caused by the muscular activity, the device being arranged to provide an alarm if the force (F) detected by the measuring transducer (3 or 13) decreases under a predetermined limit value which is as high or lower than the said preforce in order to detect a detachment of the measuring instrument.

18. The method according to claim 14 wherein the compression force (F) is observed between the points of the hand moving with respect to one another, and preferably proportional to the compression force occurring between the branches (4a,4b) of the connecting part and, correspondingly, a precompression force and a threshold compression force.

19. The method according to claim 14 wherein the method further comprises detecting the action response of muscular activity caused by electric stimulation by stimulating at least a nerve (7) of said first finger (7) for providing a signal proportional to the force caused by the movement of the first finger from the force measuring transducer (3,13) and that said first finger (7) is preferably the thumb.

20. The method according to claim 15 wherein the compression force (F) is observed between the points of the hand moving with respect to one another, and preferably proportional to the compression force occurring between the branches (4a,4b) of the connecting part and, correspondingly, a precompression force and a threshold compression force.

21. A method according to claim 16 wherein the compression force (F) is observed between the points of the hand moving with respect to one another, and preferably proportional to the compression force occurring between the branches (4a,4b) of the connecting part and, correspondingly, a precompression force and a threshold compression force.

22. A method according to claim 17 wherein the compression force (F) is observed between the points of the hand moving with respect to one another, and preferably proportional to the compression force occurring between the branches (4a,4b) of the connecting part and, correspondingly, a precompression force and a threshold compression force.

* * * * *